(12) United States Patent
Voelkel

(10) Patent No.: US 7,136,706 B1
(45) Date of Patent: Nov. 14, 2006

(54) DISTRIBUTED COMPRESSION AMPLITUDE MAPPING FOR COCHLEAR IMPLANTS

(75) Inventor: Andrew W. Voelkel, Venice, CA (US)

(73) Assignee: Advanced Bionics Corporation, Valencia, CA (US)

( * ) Notice: Subject to any disclaimer, the term of this patent is extended or adjusted under 35 U.S.C. 154(b) by 505 days.

(21) Appl. No.: 10/371,285

(22) Filed: Feb. 21, 2003

Related U.S. Application Data

(60) Provisional application No. 60/359,487, filed on Feb. 25, 2002.

(51) Int. Cl.
*A61N 1/18* (2006.01)

(52) U.S. Cl. ............................. 607/57; 607/55; 607/56

(58) Field of Classification Search ............ 607/55–57, 607/136
See application file for complete search history.

(56) References Cited

U.S. PATENT DOCUMENTS

| | | | | |
|---|---|---|---|---|
| 4,207,441 A | * | 6/1980 | Ricard et al. .................. | 607/57 |
| 4,357,497 A | * | 11/1982 | Hochmair et al. .............. | 607/5 |
| 5,603,726 A | | 2/1997 | Schulman et al. ............. | 607/57 |
| 5,749,912 A | * | 5/1998 | Zhang et al. .................. | 607/57 |
| 6,219,580 B1 | | 4/2001 | Faltys et al. .................. | 607/57 |
| 6,289,247 B1 | | 9/2001 | Faltys et al. .................. | 607/57 |
| 6,308,101 B1 | | 10/2001 | Faltys et al. .................. | 607/57 |
| 6,505,076 B1 | | 1/2003 | Tziviskos et al. ............. | 607/57 |

OTHER PUBLICATIONS

Sokolich, and Kuzma, inventors for AB-290U1; U.S. Appl. No. 10/324,183; filed Dec. 20, 2002; entitled "Wideband Low-Noise Implantable Microphone Assembly".

* cited by examiner

*Primary Examiner*—Robert E. Pezzuto
*Assistant Examiner*—Tammie K. Heller
(74) *Attorney, Agent, or Firm*—Bryant R. Gold; Victoria A. Poissant

(57) ABSTRACT

An implantable neural stimulation system, such as a cochlear implant system, utilizes a Distributed Compression Amplitude Mapping (DCAM) system to distribute signal compression between a pre-bandpass linear mapping function, and a post-bandpass compressive mapping function. The pre-bandpass linear mapping function is implemented, in one embodiment, as a traditional fast audio compressor to prevent distortion that might result from a non-linear mapping. The post-bandpass compressive mapping function is implemented, in one embodiment, as a logarithmic transform to reflect natural hearing. As a result of the DCAM processing, the differences in amplitudes of components of the acoustic spectrum are maintained. By maintaining these differences, spectral smearing between channels is reduced and speech clues are preserved.

10 Claims, 3 Drawing Sheets

DISTRIBUTED COMPRESSION AMPLITUDE MAPPING FOR COCHLEAR IMPLANTS

The present application claims the benefit of U.S. provisional application Ser. No. 60/359,487, filed Feb. 25, 2002, which application is incorporated herein by reference in its entirety, including its Appendix A.

BACKGROUND OF THE INVENTION

The present invention relates to a neural stimulator, and more particularly to a cochlear prosthesis used to electrically stimulate the auditory nerve. Even more particularly, the invention relates to an improved process for mapping a signal level into a stimulation current level.

Hearing loss, which may be due to many different causes, is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information reaches the cochlea and the hair cells. Some types of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to convert acoustic signals into auditory nerve impulses. These people are unable to derive any benefit from conventional hearing aid systems no matter how loud the acoustic stimulus is made. This is because their mechanism for converting sound energy into auditory nerve impulses has been damaged. Thus, in the absence of properly functioning hair cells, there is no way auditory nerve impulses can be generated directly from sounds.

To overcome sensorineural deafness, numerous Implantable Cochlear Stimulation (ICS) systems—or cochlear prosthesis—have been developed which seek to bypass the hair cells in the cochlea (the hair cells are located in the vicinity of the radially outer wall of the cochlea) by presenting electrical stimuli directly to the auditory nerve fibers, leading to the perception of sound in the brain and at least a partial restoration of hearing function. The common denominators in most of these cochlear prosthesis systems have been the implantation of electrodes into the cochlea, and a suitable external source of an electrical signal for the electrodes.

A cochlear prosthesis operates by direct electrical stimulation of the auditory nerve cells, bypassing the defective cochlear hair cells that normally convert acoustic energy into electrical activity in the nerve cells. In order to effectively stimulate the nerve cells, the electronic circuitry and the electrode array of the cochlear prosthesis perform the function of separating the acoustic signal into a number of parallel channels of information, each representing the intensity of a narrow frequency band within the acoustic spectrum. Ideally, the electrode array would convey each channel of information selectively to the subset of auditory nerve cells that normally transmitted signals within that frequency band to the brain. Those nerve cells are arranged in an orderly tonotopic sequence, from high frequencies at the basal end of the cochlear spiral to progressively lower frequencies towards the apex, and ideally the entire length of the cochlea would be stimulated to provide a full frequency range of hearing. In practice, this ideal is not achieved, because of the anatomy of the cochlea, which decreases in diameter from the base to the apex, and because of variations in the cochlea structure that exist between patients. Because of these difficulties, known electrodes can at best be inserted to the second turn of the cochlea.

The signal provided to the electrode array is generated by a signal processing component of the Implantable Cochlear Stimulation (ICS) system. In known ICS systems, the acoustic signal is processed by a family of parallel bandpass filters. Then, the output of each bandpass filter is independently amplitude mapped into a simulation level, using a mapping consistent with normal perception. In known systems, the mapping is a compressive mapping that is based on the log of the magnitude of the individual outputs of the band pass filters. Due to the compressive nature of the mapping, frequency bins containing large signals are reduced in amplitude much more than frequency bins containing small signals.

Representative cochlear implant systems are disclosed in U.S. Pat. Nos. 5,603,726; 6,219,580; 6,289,247 and 6,308,101; each of which patents is incorporated herein by reference.

In known ICS systems, individual stimulation channels are not well isolated from their neighbors, due both to electrical and neural interactions within the cochlea. As a result, interaction occurs between neighboring stimulus channels. Further, when signals are separated into frequency bands by the parallel bandpass filter bank, and then compressed on an individual channel basis, there is a potential for spectral contrast reduction. The spectral contrast reduction results because the channel compression reduces the amplitude of higher amplitude sounds in one frequency band more than lower amplitude sounds in another frequency band, even if both of these sounds occur simultaneously. Disadvantageously, by narrowing the amplitude differences between weak information-carrying signals and strong information-carrying signals, the spectral contrast reduction, combined with the channel interaction, can reduce the user's ability to discern the information in the strong signals.

What is needed is a compressive mapping technique which reduces the degree of compression of large signals relative to smaller signals, while still allowing for a realistic mapping of overall loudness of sound from the acoustic domain to the electrical stimulation domain.

SUMMARY OF THE INVENTION

The present invention addresses the above and other needs by providing a method for Distributed Compression Amplitude Mapping (DCAM) for Implantable Cochlear Stimulation (ICS) systems. Such DCAM method advantageously distributes signal compression between a pre-bandpass filter (which performs linear compressive mapping), and a post-bandpass filter (which performs non-linear compressive mapping). The pre-bandpass linear mapping is implemented as a traditional fast audio compressor to prevent distortion that might result from a non-linear mapping, and in a preferred embodiment comprises an envelope detector, a ballistics processor, and a gain processor to compute a scaling factor. The post-bandpass non-linear mapping is implemented as a logarithmic transform to reflect natural hearing. As a result of such DCAM processing, the differences in amplitudes of components of the acoustic spectrum are maintained.

In accordance with one aspect of the invention, large amplitude signals are protected from smearing of lower amplitude neighboring signals. The global pre-bandpass linear mapping scales the entire frequency range by a single scale factor. As such, it does not alter the relative levels of signals in different frequency bands because the same compression is applied to each frequency band. The post-bandpass compressive mapping features a reduced level of compression (made possible by the pre-bandpass compressive mapping) wherein the relative differences in magnitude between different components of the acoustic signal are maintained more than with a non-distributed compressive mapping. By maintaining the relative levels of components of the original acoustic signals, the smearing of the low level components into neighboring channels is somewhat reduced. By reducing the smearing of low level components between channels, the speech clues in the large amplitude signal components are protected.

It is a feature of the invention to provide both the benefit of a pre-bandpass linear mapping, and a logarithmic post-bandpass compressive mapping. The linear mapping provides the benefit of reducing smearing of low level channels into neighboring higher level channels. The logarithmic mapping provides signal levels that reflect natural hearing.

It is a further feature of the present invention to provide a pre-bandpass linear mapping that results in an overshoot at the output of the pre-bandpass linear mapping when sudden input transients occur. Such overshoot is similar to effects that occur in a normal ear, and thus result in more natural hearing.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The present invention provides a method for Distributed Compression Amplitude Mapping (DCAM) for Implantable Cochlear Stimulation (ICS) systems, or other neural stimulation systems. A preferred embodiment of DCAM distributes signal compression between a pre-bandpass linear compressive mapping function, and a post-bandpass non-linear compressive mapping function. The pre-bandpass mapping is implemented as a traditional fast audio compressor to prevent distortion that might result from a non-linear mapping, and in a preferred embodiment comprises an envelope detector, a ballistics processor, and a gain processor to compute a scaling factor. The post-bandpass non-linear mapping is implemented as a logarithmic transform to reflect natural hearing.

Figure 1:
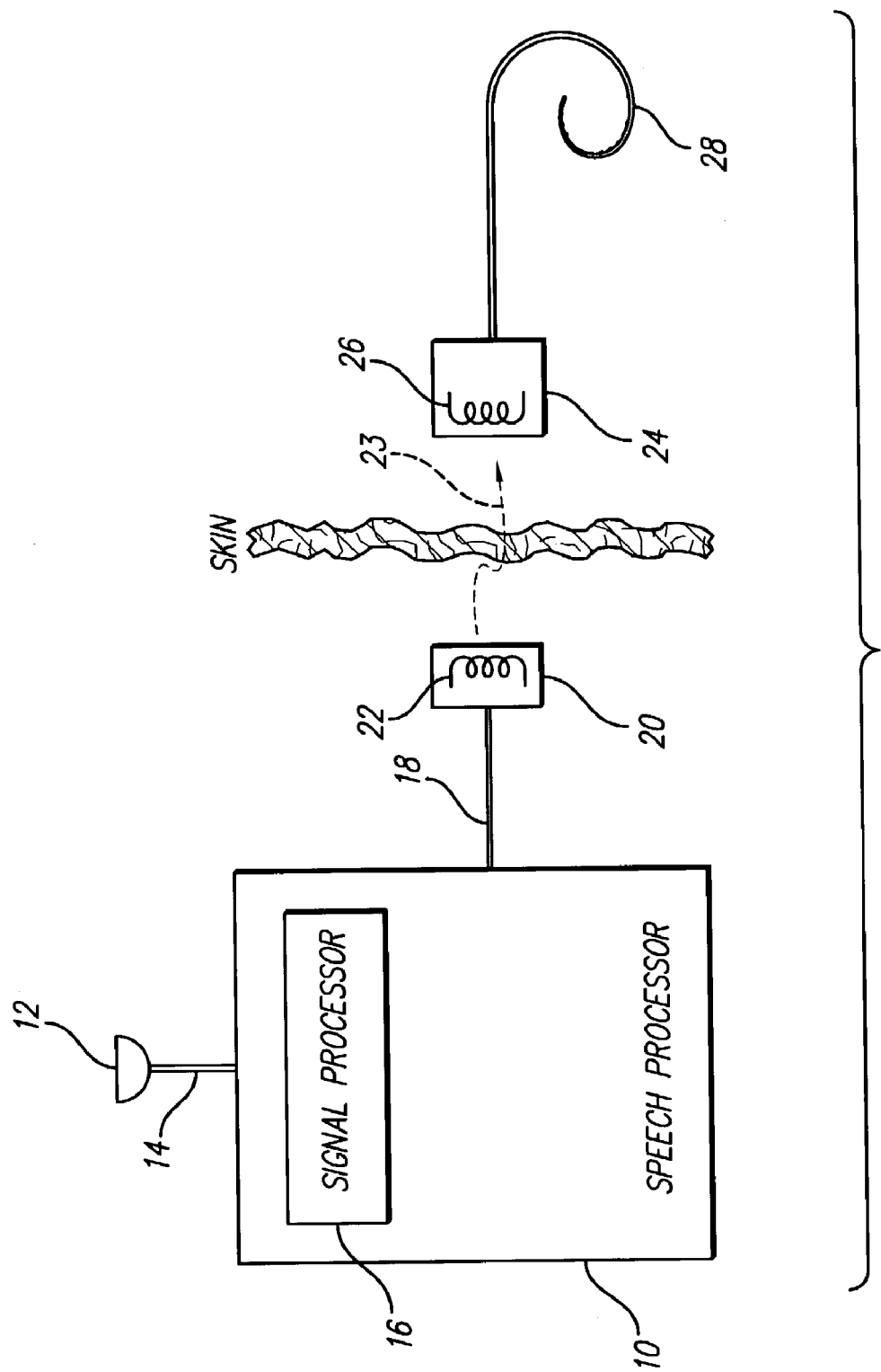
FIG. 1 shows the major elements of an Implantable Cochlear Stimulation (ICS) system.

A diagram of a typical Implantable Cochlear Stimulation (ICS) system is shown in FIG. 1. The ICS system typically includes both implanted components and external (non-implanted) components. The external components typically include a speech processor 10 that may be a wearable speech processor or a Behind-The-Ear (BTE) speech processor, or any signal processor that is used to process acoustic signals for use by the ICS system. In a fully implantable ICS system, the speech processor may be an implantable speech processor. A microphone 12 may be electrically connected to the speech processor 10 by a first lead 14, or may be incorporated into the housing of the speech processor 10, as is common in some BTE speech processors, see, e.g., U.S. Pat. No. 6,505,076, incorporated herein by reference; or as is done with some fully implantable systems, see, e.g., U.S. patent application Ser. No. 10/324,183, filed Dec. 20, 2002, also incorporated herein by reference, and assigned to same assignee as is the present application. The microphone 12 converts acoustic energy into an electrical signal having a broad spectrum for subsequent processing.

The speech processor 10 includes a signal processor 16 that processes the electrical signal from the microphone 12. The output signal of the signal processor 16 is carried by a second lead 18 to a headpiece 20 carried on the patient's head. A first coil 22 residing in the headpiece 20 couples a control signal 23 from the headpiece 20 to the implantable electronics 24, which implantable electronics 24 includes a second coil 26 for receiving the control signal. The implantable electronics 24 processes the control signal 23 and based on the information contained therein generates an appropriate stimulation current that is applied to selected electrodes of an electrode array 28. The electrode array 28 is adapted to be implanted in the patient's cochlea.

As those skilled in the art recognize, the architecture of an ICS system may vary. That is, the ICS may include a wearable speech processor that is worn on the user's belt, or carried in a user's pocket, and is connected to a microphone and a headpiece by wiring. Alternatively, the ICS system may include a Behind-The-Ear (BTE) speech processor resembling a typical hearing aid, that is worn behind the patient's ear and retained by an earhook. Another type of ICS system is a fully implantable ICS system wherein an implantable speech processor 10 is integrated into, or coupled to, an implantable stimulator. All of these variations require a microphone (or more generally a transducer), and a signal processor, to provide a stimulation level. All such variations of ICS systems, or other types of neural stimulation systems, may benefit from application of the present invention, and are intended to come within the scope of the present invention.

A human ear adjusts sound intensity using logarithmic-like scaling. Thus, if a second sound is 10 times stronger than a first sound, it may only be perceived to be twice as loud as the first sound. Known ICS systems typically perform a similar scaling, or mapping, in order for the patient to perceive sounds with a natural intensity. Additionally, such logarithmic scaling has the advantage of providing intelligible hearing for low level sounds, without overwhelming the patient when loud sounds are encountered.

Figure 2:
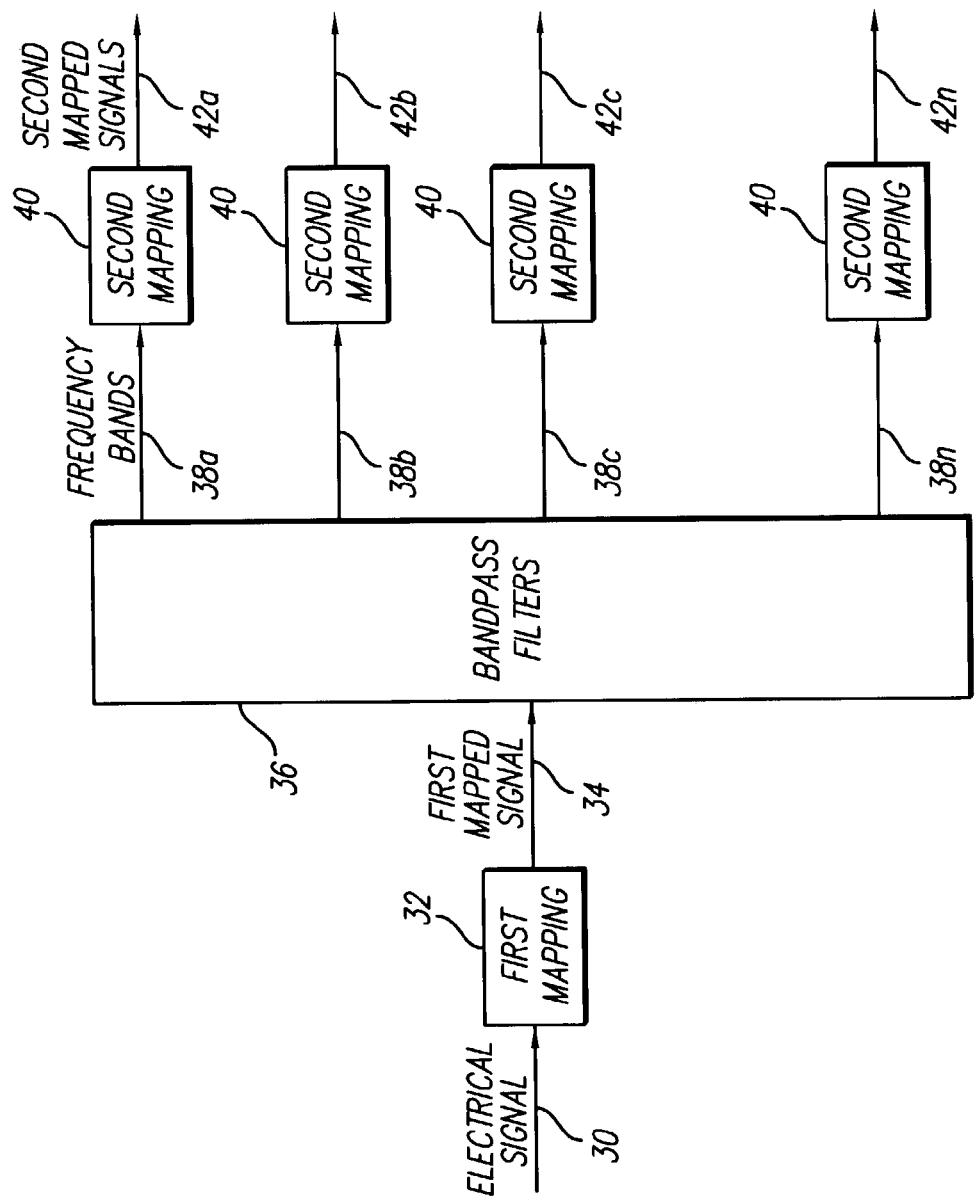
FIG. 2 shows a high level block diagram of a Distributed Compression Amplitude Mapping (DCAM) processing system made in accordance with the present invention.

A block diagram of a DCAM system made in accordance with the principles of the present invention is shown in FIG. 2. A broad spectrum electrical signal 30 is received from the microphone 12 (FIG. 1), or other transducer. The electrical signal 30 may come directly from the microphone 12, or may be pre-processed by Automatic Gain Control (AGC) circuitry, or other pre-processing circuitry. As seen in FIG. 2, the electrical signal 30 is processed by subjecting it to a first mapping function 32, resulting in a first mapped signal 34. The first mapping function 32 preferably comprises a linear compressive mapping function. However, those skilled in the art will recognize that various non-linear compressive mapping functions may also be used to produce a result comparable to that produced by the first mapping function of the present invention, and such other mapping functions are intended to come within the scope of the present invention.

The first mapped signal 34 is processed by bandpass filters 36 to produce "n" separate frequency band signals 38a–38n, where "n" represents the number of bandpass filters used during such processing. Each of the signals from the frequency bands 38a–36n are then individually processed by subjecting the respective output signal of each bandpass filter to a second mapping function 40, thereby producing a multiplicity of second mapped signals 42a–42n.

The second mapping function 40 preferably comprises a logarithmic compressive mapping function. Such logarithmic mapping may be performed in various ways. One preferred way to perform the logarithmic mapping function is to take the log of the second mapped signal on a sample by sample basis. Another way is to utilize an envelope-based second mapping function wherein a scaling function is computed at a lower data rate by taking the log of an average of every sample. Those skilled in the art will recognize that other non-linear mapping schemes, i.e, other than a log mapping, may also be used to obtain similar results.

Other methods of reducing computational requirements may likewise be implemented. For example, the elements of the second mapping function may be integrated into the bandpass filters 36 in order to improve the efficiency in, for example, FFT-based (Fast Fourier Transform-based) systems. These and other variations of the embodiment described herein are equivalent for purposes of the present invention.

As previously indicated, known ICS systems include a single mapping function to map a broad dynamic range input signal into a stimulation level suitable for stimulating the cochlea. In contrast, the heart of the present invention is the distribution of the single mapping function into the first mapping function 32 and the second mapping function 40. It is noted that the combined result of the first mapping function 32 and second mapping function 40, for any steady state sine wave input, is substantially identical to the result from a known single mapping. However, where the input is not a steady state sine wave, as is most always the case for a cochlear implant system, then the advantages of distributing the mapping function as described herein are achieved.

Figure 3:
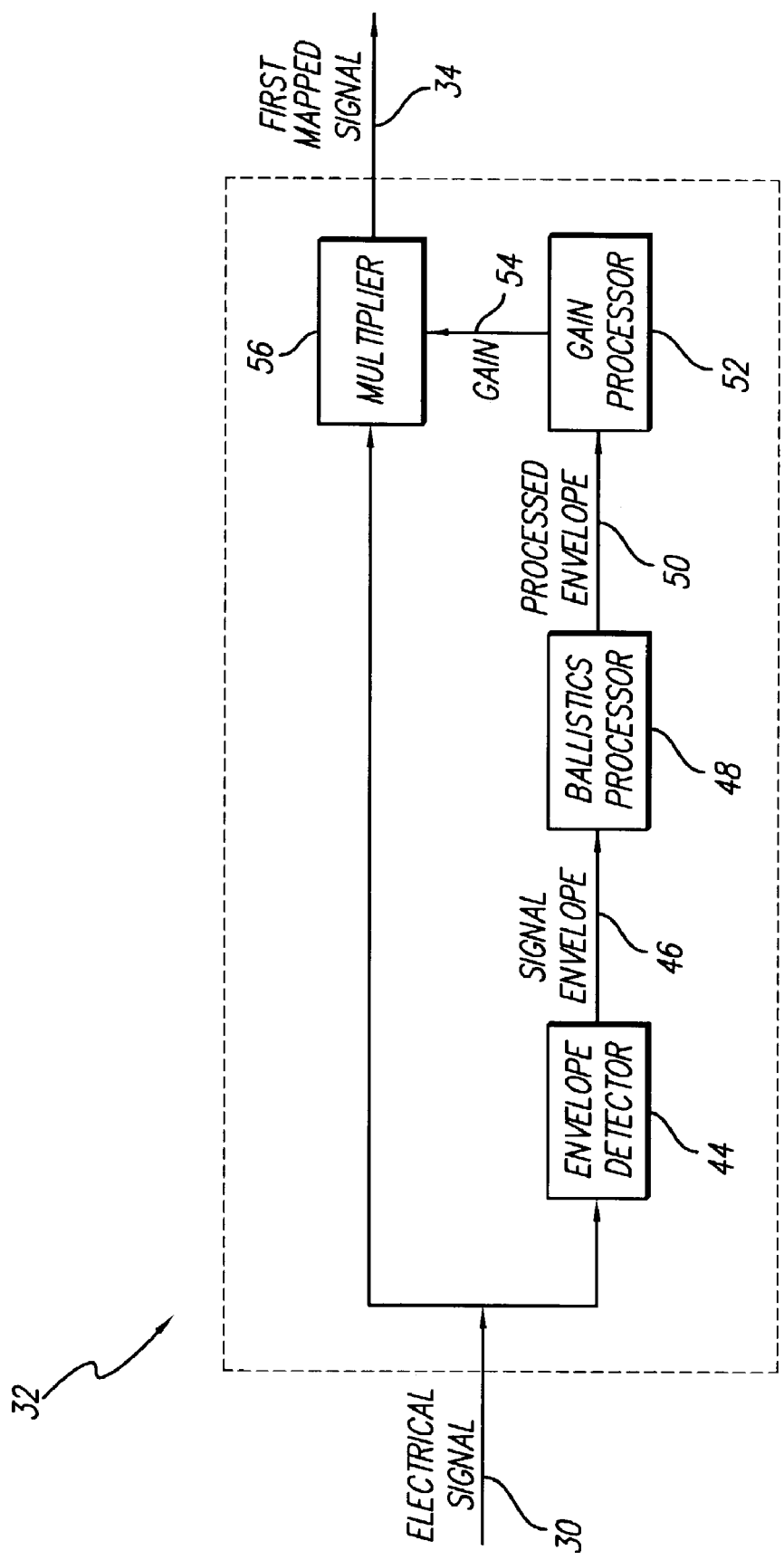
FIG. 3 shows a block diagram of one embodiment of a first mapping scheme that may be used as part of the DCAM processing system shown in FIG. 2.

One preferred embodiment of the processing performed by the first mapping function 32 is depicted in FIG. 3. The electrical signal 30 is shared between two paths. A first path carries the electrical signal 30 in an unaltered form to a multiplier circuit 56. A second path processes the electrical signal 30 to generate a gain signal 54. The first processing step or element encountered in the second path is an envelope detector 44. The envelope detector 44 generates a "signal envelope" output signal 46. The signal envelope output signal 46 is then processed by a ballistics processor circuit 48, explained more fully below to produce a processed envelop signal 50. The processed envelop signal 50 is then processed by a gain processor 52 to generate a gain signal 54. The original electrical signal 30 is multiplied by the gain signal 54 by the multiplier circuit 56. The output signal from the multiplier circuit 56 comprises the first mapped signal 34. The gain signal 54 may be generated at the sample rate, or more slowly, depending on the implementation.

The envelope detector 44 preferably comprises a full wave rectifier circuit followed by a lowpass filter. The filter cutoff frequency is preferably about 40 Hz, but other frequencies may be selected as well to block any audio frequencies present in the rectified signal, which in a particular ICS system may be determined by experimentation. Further, to some extent, the ballistics processor 48 may function as a lowpass filter for the envelope detector. Those of skill in the art will recognize other types of equivalent envelope detectors, such as an RMS detector, where the rectifier is replaced by a squaring function, the filter is replaced by an averager circuit (that computes the average over a certain time period), and the square root of the averager circuit output is the envelope signal.

The ballistics processor 48 allows for control over the attack and decay times of the compressor. That is, the ballistics processor 48 transforms the signal envelop 46 obtained from the envelope detector 44 into a processed envelope 50 which is provided to the gain processor 52. The ballistics processor 48 limits the rate at which the processed envelope signal 50 is allowed to follow the signal envelop 46. If the signal envelope 46 is greater than the processed envelope signal 50, the processor is considered to be in the 'attack' mode. If the signal envelop 46 is lower than the processed envelope signal 50, the processor is considered to be in 'release mode'. In a simple compressor, the same equation is used to determine the processed envelope 50 in both modes:

$$C_{(n)} = C_{(n-1)} + (Env_{(n)} - C_{(n-1)}) * \lambda \qquad (1)$$

where $Env_{(n)}$ is the current value of the signal envelop 46, $C_{(n-1)}$ is the previous value of the processed envelope 50, and $C_{(n)}$ is the new value of the processed envelope 50. The value of $\lambda$ depends on the mode (i.e., attack mode or release mode). In the attack mode, a preferred value of $\lambda$ is about 0.2, and in the release mode, a preferred value of $\lambda$ is about 0.0018.

The gain processor 52 determines the magnitude of the gain signal 54 used to scale the electrical signal 30 in accordance with equations (2) and (3):

$$G(C) = \left(\frac{C}{C_0}\right)^{(\frac{1}{M}-1)} \cdot G_0, \text{ if } C > C_0 \qquad (2)$$

$$G(C) = 1, \text{ otherwise} \qquad (3)$$

where G(C) is the gain signal 54, and M is the compression ratio:

$$M = IDR\_B/IDR \qquad (4)$$

where IDR is the Input Dynamic Range, preferably 70 dB, and IDR_B is the Input Dynamic Range after the First Mapping 32, and is preferably about 50. The parameter "C" was defined for equation (1) above, $C_0$ is the threshold, and is set to be equal to the floor of the dynamic range, and as a result, $C_0$ is preferably about −70 dB.

A gain signal 54 used by the first mapping function 32 of the DCAM processing is provided by the gain processor 52. The signal provided to the log mapper of known ICS systems is typically in the range of −70 dB to 0 dB (i.e., a signal level of 0.000316 to 1.0). The objective of having the gain signal 54 is preferably to linearly map the signal into a −50 dB to 0 db range (i.e., a signal level of 0.00316 to 1.0).

Those skilled in the art will recognize that while the first mapping function 32 is described as a separate process from the AGC, the two may be combined into a single process. Similarly, the second mapping function 40 could be combined with the bandpass filters. These and other variations are intended to some within the scope of the present invention.

Those of skill in the art will also recognize that the functions shown in the block diagrams of FIGS. 2 and 3 are just that—functions. Such functions, as has already been indicated, may be performed or carried out in various ways, including using hardware circuits, programmed processors (i.e., via software), and through various combinations of hardware and software.

The first mapped output signal 34 produced by the first mapping function 32 is processed by the bandpass filters 36, as shown in FIG. 2. The bandpass filters 36 produce the frequency band signals 38a–38n, each of which is subjected to a respective second mapping function 40a–40n. A preferred second mapping transform curve maps the frequency bands 38a–38n from a range of −50 dB to 0 db range (i.e., a signal level of 0.00316 to 1.0) into a stimulation range measured for each patient. The second mapping is of the form:

$$\text{output} = A * \log(\text{input}) + K \tag{5}$$

Typically, the stimulation range will be from a Threshold (T) level of 50 to 100 µa (microamps), to a Most Comfortable Level (MCL) of 200 µa to 500 µa. The threshold and most comfortable level for each patient are measured individually, and used to compute the parameters A and K:

$$A = (MCL - T)/(\log(\text{max input}) - \log(\text{min imput})) \tag{6}$$

$$K = T - A * \log(\text{min input}) \tag{7}$$

where:
max input=1.0 (preferred value)
min input=0.00316 (preferred value)

Equations (6) and (7) may be solved to determine the parameters A and K for each particular patient and for a specified range of input signal values, in this case, from a minimum input of about 0.00316 to a maximum input of about 1.0. The second mapping function thus involves using the resulting values for A and K in equation (5). The values of A and K that result from reducing the range of input values of the second mapped signals 40a–40n, from the range of about −70 dB to 0 dB to the range of about −50 dB to 0 dB, cause the amount of compression of signals processed by the second mapping function 40a–40n to be reduced.

Those skilled in the art will recognize that other compressive mapping functions may be substituted for the non-linear second compressive mapping function contemplated by equation (5). The range of inputs applied to the non-linear second compressive mapping function may also be varied to achieve the best performance for a given patient and a given ICS system. A key feature of the present invention is to distribute the compressive mapping in known ICS systems between a linear first compressive mapping function and a non-linear second compressive mapping function in order to narrow the range of input signals to the non-linear second compressive mapping. The result is a decrease in the compression of frequency bands, including large amplitude signals. Any combination of a linear first compressive mapping and a non-linear second compressive mapping that achieves this goal is intended to come within the scope of the present invention.

While the invention herein disclosed has been described by means of specific embodiments and applications thereof, numerous modifications and variations could be made thereto by those skilled in the art without departing from the scope of the invention set forth in the claims.

What is claimed is:

1. A distributed amplitude mapping method for an Implantable Cochlear Stimulation (ICS) system, comprising:
    performing a first mapping function to generate a first mapped signal by compressing a broad spectrum electrical input signal; and
    performing a second mapping function following the first mapping function wherein individual frequency bands within the first mapped signal are subjected to the second mapping function;
    wherein performing a first mapping function comprises performing a mapping function using an audio compressor, wherein using the audio compressor comprises:
        performing envelope detection on the broad spectrum electrical input signal to produce an envelope detection output signal;
        performing ballistics processing on the envelope detection output signal to produce a ballistics processing output signal;
        performing gain processing on the ballistics processing output signal to produce a gain processing output signal; and
        multiplying the gain processing output signal by the broad spectrum electrical input signal to produce the first mapped signal.

2. The method of claim 1 wherein performing the first mapping function further includes filtering the first mapped signal into frequency bands to produce a filtered output signal for each frequency band, and wherein performing the second mapping function following the first mapping function comprises performing the second mapping function on each of the filtered output signals for each frequency band.

3. The method of claim 1 wherein performing a first mapping function comprises performing a linear mapping function.

4. The method of claim 1 wherein performing the second mapping function comprises performing a non-linear mapping function.

5. The method of claim 1 wherein performing the second mapping function comprises performing a compressive mapping function.

6. The method of claim 5 wherein performing the second mapping function comprises performing a logarithmic mapping function.

7. A distributed amplitude mapping method for an Implantable Cochlear Stimulation (ICS) system, comprising:
    performing a linear first mapping function to generate a first mapped signal by compressing a broad spectrum electrical input signal; and
    performing a non-linear second mapping function following the linear first mapping function wherein individual frequency bands within the first mapped signal are subjected to the non-linear second mapping function to generate a second mapped signal, wherein performing the linear first mapping function comprises performing a mapping function using an audio compressor wherein using the audio compressor comprises:
- performing envelope detection on the broad spectrum electrical input signal to produce an envelope detection output signal;
- performing ballistics processing on the envelope detection output signal to produce a ballistics processing output signal;
- performing gain processing on the ballistics processing output signal to produce a gain processing output signal; and
- multiplying the gain processing output signal by the broad spectrum electrical input signal to produce the first mapped signal.

8. The method of claim 7 wherein performing the linear first mapping function further includes filtering the first mapped signal into frequency bands to produce a filtered output signal for each frequency band, and wherein performing the non-linear second mapping function following the first mapping function comprises performing the second mapping function on each of the filtered output signals for each frequency band.

9. The method of claim 7 wherein performing the non-linear mapping function comprises performing a compressive mapping function.

10. The method of claim 9 wherein performing the non-linear mapping function comprises performing a logarithmic mapping function.

* * * * *